US011135456B2

(12) United States Patent
Copeland et al.

(10) Patent No.: US 11,135,456 B2
(45) Date of Patent: Oct. 5, 2021

(54) HAND SANITIZERS WITH IMPROVED AESTHETICS AND SKIN-CONDITIONING TO ENCOURAGE COMPLIANCE WITH HAND HYGIENE GUIDELINES

(71) Applicant: GOJO INDUSTRIES, INC., Akron, OH (US)

(72) Inventors: Amanda J. Copeland, Seville, OH (US); Jessica Rae Tittl, Chagrin Falls, OH (US); Abel Saud, Loveland, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 14/657,447

(22) Filed: Mar. 13, 2015

(65) Prior Publication Data
US 2015/0258003 A1  Sep. 17, 2015

Related U.S. Application Data

(60) Provisional application No. 61/953,034, filed on Mar. 14, 2014.

(51) Int. Cl.
| A61Q 19/00 | (2006.01) |
| A61K 8/34 | (2006.01) |
| A61K 8/42 | (2006.01) |
| A61K 8/49 | (2006.01) |
| C11D 17/08 | (2006.01) |
| C11D 7/26 | (2006.01) |
| A61Q 17/00 | (2006.01) |
| C11D 7/32 | (2006.01) |
| A61K 8/66 | (2006.01) |

(52) U.S. Cl.
CPC .............. *A61Q 19/007* (2013.01); *A61K 8/34* (2013.01); *A61K 8/42* (2013.01); *A61K 8/4926* (2013.01); *A61K 8/66* (2013.01); *A61Q 17/005* (2013.01); *C11D 7/261* (2013.01); *C11D 7/3272* (2013.01); *C11D 17/08* (2013.01)

(58) Field of Classification Search
None
See application file for complete search history.

(56) References Cited

U.S. PATENT DOCUMENTS

| 4,956,170 A | 9/1990 | Lee | |
| 5,690,918 A * | 11/1997 | Jacks | A61K 8/4913 424/401 |
| 5,939,082 A | 8/1999 | Oblong et al. | |
| 6,183,766 B1 * | 2/2001 | Sine | A61K 8/0208 424/401 |
| 6,277,364 B1 | 8/2001 | Bucks et al. | |
| 6,319,958 B1 | 11/2001 | Johnson et al. | |
| 6,534,069 B1 | 3/2003 | Asmus et al. | |
| 6,607,737 B2 | 8/2003 | Bekele et al. | |
| 6,613,341 B2 | 9/2003 | Motley et al. | |
| 6,753,020 B1 | 6/2004 | Mayne et al. | |
| 6,818,232 B1 * | 11/2004 | Redmond | A23L 1/3051 424/750 |
| 7,018,623 B2 | 3/2006 | Barclay et al. | |
| 7,175,850 B2 | 2/2007 | Ceve et al. | |
| 7,591,949 B2 | 9/2009 | Ceve et al. | |
| 7,651,990 B2 | 1/2010 | Asmus | |
| 7,803,390 B2 | 9/2010 | Asmus et al. | |
| 7,820,720 B2 | 10/2010 | Ceve | |
| 7,879,344 B2 | 2/2011 | Feldkamp et al. | |
| 7,879,372 B2 | 2/2011 | Yoshpe et al. | |
| 7,887,823 B2 | 2/2011 | Redmond et al. | |
| 8,057,830 B2 | 11/2011 | Brumbaugh et al. | |
| 8,058,315 B2 | 11/2011 | Wegner et al. | |
| 8,124,115 B2 | 2/2012 | Veeger et al. | |
| 8,203,016 B2 | 6/2012 | Schmaus et al. | |
| 8,236,288 B2 | 8/2012 | Mehta et al. | |
| 8,263,098 B2 | 9/2012 | Fernandez de Castro | |
| 8,304,375 B1 | 11/2012 | Wolff et al. | |
| 8,309,111 B2 | 11/2012 | Fernandez de Castro | |
| 8,313,758 B2 | 11/2012 | Fernandez de Castro | |
| 8,333,954 B2 | 12/2012 | Seldling et al. | |
| 8,383,686 B2 | 2/2013 | Wegner et al. | |
| 8,409,552 B2 | 4/2013 | Schmaus et al. | |
| 8,461,207 B2 | 6/2013 | Aydt et al. | |
| 8,512,719 B2 | 8/2013 | Redmond et al. | |

(Continued)

FOREIGN PATENT DOCUMENTS

| CA | 2130284 A1 | 3/1995 |
| EP | 0640285 A1 | 3/1995 |

(Continued)

OTHER PUBLICATIONS

International Search Report dated Jul. 15, 2015, for International Patent Application No. PCT/US2015/020481.
"WHO Guidelines on Hand Hygiene in Health Care: a Summary," pp. 1-52, World Health Organization (Jul. 2009).
Baumann, L.S., "Avenanthramides Continue the Evolution of Dermatologic Use of Oat Products," A Supplement to Skin & Allergy News, Cosmeceutical Critique Compendium, A Review of Natural Ingredients, pp. 1-4, Elsevier (Feb. 14, 2008).
Vollhardt, J., D.A. Fielder, and M.J. Redmondt, "Identification and Cosmetic Application of Powerful Anti-Irritant Constituents of Oat Grain," pp. 395-402, Proceedings, XXI IFSCC International Congress 2000, Berlin (2000).

(Continued)

Primary Examiner — Katherine Peebles
(74) Attorney, Agent, or Firm — Calfee, Halter & Griswold LLP

(57) ABSTRACT

Hand sanitizers are provided with improved aesthetics and skin-conditioning effects, such that healthcare workers and others subject to high frequency hand hygiene requirements are encouraged to comply with said requirements. The hand sanitizers provide excellent antimicrobial efficacy and skin conditioning benefits that actually increase with increased frequency of use. The sanitizing compositions are hydroalcoholic, and contain a synergistic combination of skin-conditioning agents.

2 Claims, 1 Drawing Sheet

(56) References Cited

U.S. PATENT DOCUMENTS

| | | |
|---|---|---|
| 8,530,524 B2 | 9/2013 | Wegner et al. |
| 2006/0204466 A1 | 9/2006 | Littau et al. |
| 2006/0204467 A1 | 9/2006 | Littau et al. |
| 2007/0148101 A1* | 6/2007 | Snyder .................. C11D 1/008 424/47 |
| 2010/0216892 A1* | 8/2010 | Schmaus ................ A61K 8/345 514/738 |
| 2010/0261795 A1* | 10/2010 | Buzot .................. A61K 9/0014 514/568 |
| 2010/0267662 A1* | 10/2010 | Fielder ................ A61K 31/196 514/54 |
| 2011/0144213 A1* | 6/2011 | Mallard ................ A61K 8/347 514/721 |
| 2011/0195112 A1* | 8/2011 | Orvar ...................... A61K 8/64 424/450 |
| 2011/0201693 A1 | 8/2011 | Littau et al. |
| 2011/0202071 A1* | 8/2011 | Smith .................... A45D 26/00 606/133 |
| 2011/0237674 A1* | 9/2011 | Zhang .................. A61K 31/165 514/567 |
| 2012/0208894 A1 | 8/2012 | Guenter |
| 2013/0177504 A1 | 7/2013 | Macoviak |
| 2013/0224273 A1 | 8/2013 | Redmond et al. |
| 2013/0230610 A1 | 9/2013 | Redmond et al. |

FOREIGN PATENT DOCUMENTS

| | | |
|---|---|---|
| JP | 2003-267862 A | 9/2003 |
| WO | 0067626 A2 | 11/2000 |
| WO | 0071093 A1 | 11/2000 |
| WO | 2006085907 A2 | 8/2006 |
| WO | 2006096239 A1 | 9/2006 |
| WO | 2012163928 A2 | 12/2012 |

OTHER PUBLICATIONS

Visscher, M., J. Davis, and R. Wickett, "Effect of Topical Treatments on Irritant Hand Dermatitis in Health Care Workers," pp. 1-9, American J. of Infection Control vol. 37,10, p. 842.e1-842.e11 (Dec. 2009).

Visscher, M., "Overcoming Barriers to Hand Hygiene Compliance," pp. 46-59, Managing Infection Control (May 2009).

Ertel, K., Bruce H. Keswick, and Paula B. Bryant, "A Forearm Controlled Application Technique for Estimating the Relative Mildness of Personal Cleansing Products," pp. 67-76, Journal of the Society of Cosmetic Chemists, vol. 46, (Mar./Apr. 1995).

Maryanne McGuckin, et al., Hand Hygiene Compliance Rates in the United States—A One-Year Multicenter Collaboration Using Product/Volume Usage Measurement and Feedback, American Journal of Medical Quality, 2009, vol. 24, No. 3, pp. 205-213.

M.O. Visscher, et al., Hand Hygiene Compliance and Irritant Dermatitis: a Juxtaposition of Healthcare Issues, International Journal of Cosmetic Science, 2012, vol. 34, pp. 402-415.

John M. Boyce, et al., Skin Irritation and Dryness Associated With Two Hand-Hygiene Regiments: Soap-and-Water Hand Washing Versus Hand Antisepsis With an Alcohol Hand Gel, Infection Control and Hospital Epidemiology, 21(7):442-8, Jul. 2000.

Food and Drug Administration, Tentative Final Monograph for Healthcare Antiseptic Drug Products: proposed rule. Fed. Reg. 59:31441-31452, Jun. 17, 1994.

Quigley J W, Bucks DAW: "Reduced skin irritation with tretinoin containing polyolprepolymer-2, a new topical tretinoin delivery system: A summary of preclinical and clinical investigations", J Am Acad Dermatol, vol. 38 Apr. 1, 1998 (Apr. 1, 1998), Apr. 1, 1998 (Apr. 1, 1998), pp. S5-S10, XP055481587.

\* cited by examiner

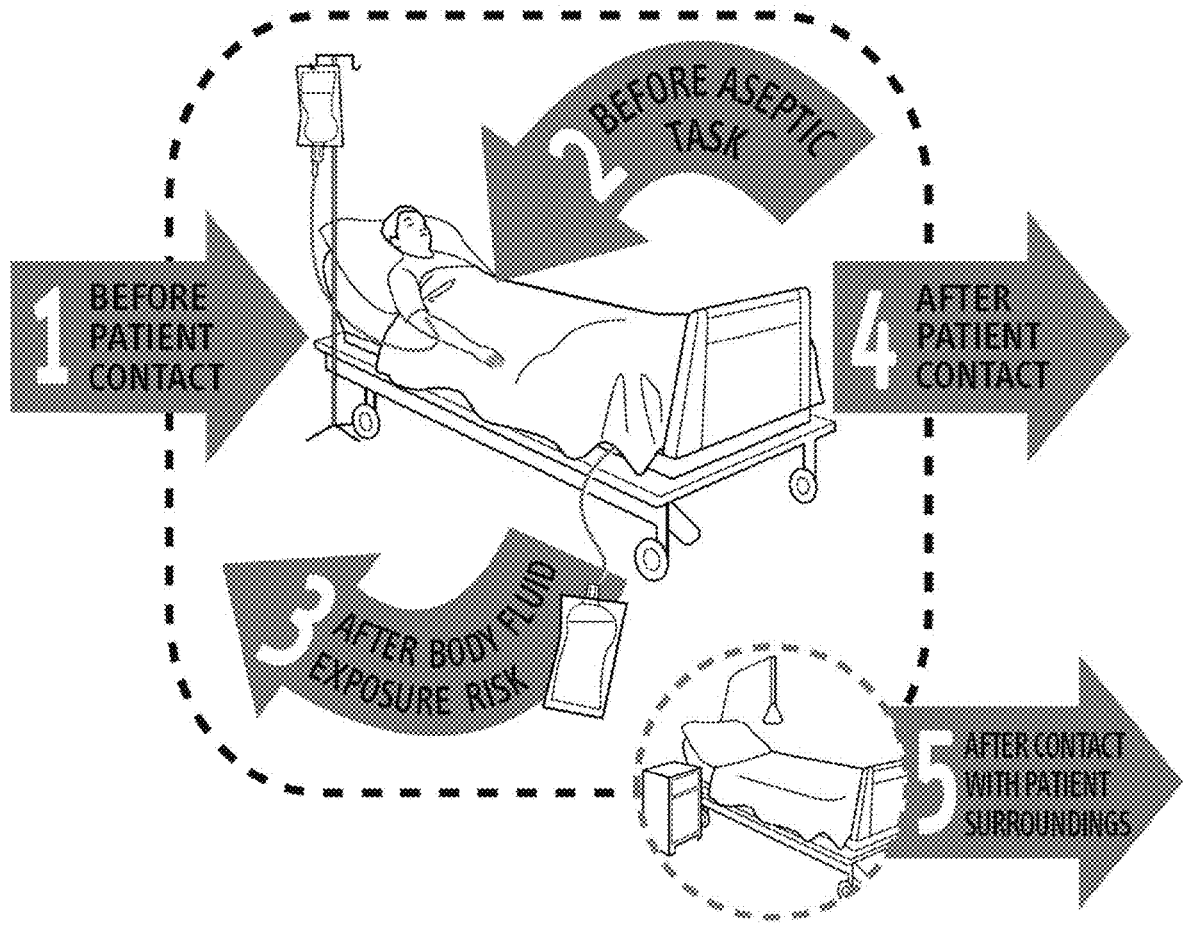

HAND SANITIZERS WITH IMPROVED AESTHETICS AND SKIN-CONDITIONING TO ENCOURAGE COMPLIANCE WITH HAND HYGIENE GUIDELINES

RELATED CASES

This application claims priority from U.S. Provisional Patent Application Ser. No. 61/953,034 filed on Mar. 14, 2014, which is hereby incorporated by reference.

TECHNICAL FIELD

One or more embodiments of the present invention provide hand sanitizers with improved aesthetics and skin-conditioning effects, such that healthcare workers and others subject to high frequency hand hygiene requirements are encouraged to comply with said requirements. One or more embodiments of the present invention provide excellent antimicrobial efficacy and skin conditioning benefits that actually increase with increased frequency of use.

BACKGROUND OF THE INVENTION

Hand hygiene is the primary measure to reduce infections. Most hospitals and health-care facilities have established hand hygiene guidelines that require frequent use of hand sanitizers and hand washes. Lack of compliance among health-care providers is problematic worldwide.

Adherence of health care workers to recommended hand hygiene procedures has been reported as variable. In observational studies conducted in hospitals, health care workers cleaned their hands on average from 5 to as many as 42 times per shift and 1.7 to 15.2 times per hour. In addition, the duration of hand cleansing episodes ranged on average from as short as 6.6 seconds to 30 seconds. A common self-reported factor for poor adherence with hand hygiene is that hand hygiene agents cause irritations and dryness. In fact, some studies have concluded that the primary reason for non-compliance is skin irritation and the deleterious effects of repeated exposure to products and procedures.

Skin exposure to water and typical cleansers has profound effects on the stratum corneum (SC) structure and function. Effects include disruption of the lipid bilayer architecture to create defects or holes in the barrier. As a result, the barrier becomes more permeable, allowing irritants and microorganisms to penetrate into and through the uppermost layers of the skin. In cases of severe hand irritation, cracks or fissures (with or without bleeding) may develop indicating damage to the dermis. The skin's response to these damaging effects is immediate, but the accelerated efforts to repair the barrier and generate new stratum corneum leads to imperfect architecture, when compared to stratum corneum that is formed during the normal course of SC replacement. The rapidly-produced SC has poor water binding properties, leading to insufficient skin moisture and inadequate desquamation.

Under normal conditions, there is constant loss of SC cells, as individual units from the surface of the skin, and new cells move from the bottom of the SC to the surface, generally over a period of about 14 days. When skin moisture is too low, the SC cells come off of the skin surface as clumps of cells, observed as dry scales.

In some studies, up to 85 percent of nurses described histories of skin problems and one-fourth reported symptoms of dermatitis. Over half of inpatient nurses, and 65 percent in intensive care units had observable hand dermatitis.

A study has been done on the effect of various alcohols on skin under conditions of frequent hand sanitization. Few environments are impacted more by topical product usage than healthcare facilities. As high Hand Hygiene Compliance (HHC) and Alcohol-Based Hand Rub (ABHR) together play a significant role in healthcare strategies to reduce the threat of nosocomial infections, Healthcare Workers (HCW) may be subjected to significant increases in the use of ABHR. As handwashing opportunities ranging from less than 20 times per hour (reflecting 58% Compliance) to more than 60 per hour (reflecting 37% Compliance) are being challenged as insufficient to meet recommended guidelines, Hand Hygiene Events (HHE) rates approaching 100 per day may be necessary to achieve 100% HHC.

The study compared the effects three different alcohol systems have on skin over two weeks, applied daily at standard and high frequency HHC for HCWs application. Twenty five female panelists representing a typical healthcare worker demographic were recruited for a two week Forearm Control Application Test (FCAT). The study commenced with a one week washout period of the forearms using a commercially available gentle foam cleanser. Visual Redness was scored based upon a scale—"Severe Redness" (Scale 0 "No Redness" to 6 "Extreme Redness"). Panelists exhibiting Visual Redness or Dryness score at any treatment site greater than 3.0 at baseline were excluded from participation. This was followed by regimen treatments and skin assessments conducted at regular intervals over the two week evaluation. Three ABHR systems containing 70% alcohol (each ethanol, isopropanol, and n-propanol), water, and a minimal humectant (0.2% glycerin) were used. Panelist forearms were marked to receive the randomized regimens: three alcohol systems applied at 20 times per day (standard frequency; SF); three alcohol systems applied at 100 times per day (high frequency HF); and an untreated skin control. In addition to the test regimens, panelist's forearms were washed six times per day at scheduled intervals of a minimal HCW daily routine. Skin redness and dryness (Visual Grading), skin hydration (Corneometer CM825), and skin barrier or trans-epidermal water loss (TEWL/Biox AquaFlux AF200) were measured. Following a total of 200 (SF), and 1000 (HF) individual alcohol system applications and corresponding skin measures, data were tabulated and analyzed. Analysis of variance (ANOVA) was used to assess the individual and interactive effects of alcohol type and application rate, and to compare to the untreated skin control. Chi-Square analysis was also used to evaluate the regimen attrition due to skin condition meeting predetermined thresholds. The study confirmed that higher levels of HHC can further compromise the already challenged skin condition of HCW.

There is a substantial need for practices and products that disinfect the skin surface without compromising the integrity of the skin barrier. Products and practices are needed that improve or at least maintain skin condition of healthcare workers who use ABHRs many times a day.

SUMMARY OF THE INVENTION

Embodiments of the present invention provide a composition comprising at least one $C_{1-6}$ alcohol, and at least one primary skin conditioning agent.

Embodiments of the present invention provide a composition comprising at least one $C_{1-6}$ alcohol, at least one primary skin conditioning agent, and a deposition enhancer.

Embodiments of the present invention provide a composition comprising at least one $C_{1-6}$ alcohol, at least one phytochemical with anti-inflammatory properties, at least one and enzyme or coenzyme that aids in the formation of the stratum corneum, and a deposition enhancer.

Embodiments of the present invention provide an effective healthcare personnel handwash composition that maintains or improves skin hydration, the composition comprising from about 10 to about 98 percent by weight (wt. %) of at least one $C_{1-6}$ alcohol, based upon the total weight of the composition, at least one phytochemical with anti-inflammatory properties, at least one enzyme or coenzyme that aids in the formation of the stratum corneum, and at least one deposition enhancer selected from the group consisting of polyolprepolymer-2, polyolprepolymer-14, and polyolprepolymer-15.

Embodiments of the present invention further provide a method for improving skin condition of health care workers within 3 days, the method comprising the steps of providing a composition according to any of the preceding claims, providing a health care worker with a need to sanitize their hands at least 50 times during a work shift, applying the composition to the hands of the health care worker at least 50 times during the work shift, wherein the health care worker works at least 3 shifts during 3 consecutive days.

Embodiments of the present invention include a method for improving the aesthetics and skin hydration efficacy of an alcoholic skin sanitizing composition, the method comprising the steps of combining from about 50 to about 98 wt. % of a $C_{1-6}$ alcohol, from about 0.001 to about 8 wt. % of a phytochemical with anti-inflammatory properties; from about 0.001 to about 8 wt. % of an enzyme or coenzyme that aids in the formation of the stratum corneum; and from about 0.005 to about 10 wt. % of a deposition enhancer selected from the group consisting of surfactants, bile salts, fatty acids, chelating agents, and sulphoxides to form an alcoholic skin sanitizing composition, with the proviso that the total amount of phytochemicals with anti-inflammatory properties and enzymes or coenzymes that aid in the formation of the stratum corneum is no more than 10 wt. %, based upon the total weight of the composition, with the proviso that the composition includes only from zero to about 2 total wt. % of any skin-conditioning agent other than said phytochemicals with anti-inflammatory properties; said enzyme or coenzyme that aids in the formation of the stratum corneum, based upon the total weight of the composition, wherein the composition exhibits less tackiness than the same composition but containing greater than about 2 total wt. % of any skin-conditioning agent other than said phytochemicals with anti-inflammatory properties; said enzyme or coenzyme that aids in the formation of the stratum corneum; and said deposition enhancer, based upon the total weight of the composition; and wherein the composition exhibits improved skin hydration with multiple uses.

Embodiments of the present invention further provide a method for improving skin condition of health care workers within 3 consecutive days, the method comprising the steps of providing a composition as described herein, applying the composition to the hands of the health care worker at least 50 times during a 24-hour day, and repeating the step of applying the composition to the hands of the health care worker on at least two additional 24-hour days within a total period of 3 consecutive days.

BRIEF DESCRIPTION OF THE DRAWINGS

FIG. 1 is a schematic depiction of the five moments for hand hygiene in health care, according to the World Health Organization publication entitled "WHO Guidelines on Hand Hygiene in Health Care: a Summary" p. 27 (2009).

DETAILED DESCRIPTION OF ILLUSTRATIVE EMBODIMENTS

I. General

The form of the compositions of the present invention is not particularly limited. In one or more embodiments, compositions of the present invention may be formulated as a foamable composition, a thickened gel composition, a sprayable liquid, a rinse, or may be applied to a wipe.

Generally, compositions of the present invention are antimicrobial hydroalcoholic compositions that include a synergistic combination of skin conditioning agents. Synergistic refers to, for example, the synergistic improvement in hydration of the skin and improvement in skin barrier function that is seen with repeated use of compositions of the present invention, when compared to antimicrobial hydroalcoholic compositions that do not include the primary skin conditioning agents described herein.

II. Alcohol

In one or more embodiments, the alcohol is a $C_{1-6}$ alcohol, i.e. an alcohol containing 1 to 6 carbon atoms. Such alcohols may be referred to as lower alkanols. Typically, these alcohols have antimicrobial properties. Examples of lower alkanols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the compositions comprise a mixture of alcohols. In one or more embodiments, the compositions comprise a mixture of ethanol and isopropanol. In one or more embodiments, the compositions comprise a mixture of isopropanol and n-propanol.

Generally, the composition comprises at least about 30 percent by weight (wt. %) alcohol, based upon the total weight of the composition. In one embodiment, the composition comprises at least about 35 wt. % alcohol, in another embodiment, the composition comprises at least about 40 wt. % alcohol, in another embodiment, the composition comprises at least about 50 wt. % alcohol, in another embodiment, the composition comprises at least about 60 wt. % alcohol, in another embodiment, the composition comprises at least about 65 wt. % alcohol, in yet another embodiment, the composition comprises at least about 70 wt. % alcohol, and in still yet another embodiment, the composition comprises at least about 78 wt. % alcohol, based upon the total weight of composition. More or less alcohol may be required in certain instances, depending particularly on other ingredients and/or the amounts thereof employed in the composition. In certain embodiments, the composition comprises from about 10 wt. % to about 98 wt. % alcohol, in other embodiments, the composition comprises from about 15 wt. % to about 95 wt. % of alcohol, in yet other embodiments, the composition comprises from about 20 wt. % to about 90 wt. % of alcohol, and in still other embodiments, the composition comprises from about 30 wt. % to about 85 wt. % of alcohol, based upon the total weight of the composition. In certain embodiments, the composition comprises from about 50 wt. % to about 98 wt. % alcohol, in other embodiments, the composition comprises from about 60 wt. % to about 95 wt. % of alcohol, in yet other embodiments, the composition comprises from about 65 wt. % to about 90 wt. % of alcohol, and in still other embodiments, the composition comprises from about 70 wt. % to about 85 wt. % of alcohol, based upon the total weight of the composition.

III. Primary Skin-Conditioning Agents

Embodiments of the present invention include one or more primary skin-conditioning agents. Primary skin-conditioning agents include phytochemical with anti-inflammatory properties and enzymes or coenzymes that aid in formation of the stratum corneum.

In one or more embodiments, compositions of the present invention include at least one phytochemical with anti-inflammatory properties. In one or more embodiments, compositions of the present invention include at least one enzyme or coenzyme that aids in the formation of skin stratum corneum. Advantageously, it has been discovered that the combination of a phytochemical with anti-inflammatory properties and an enzyme or coenzyme that aids in the formation of the stratum corneum provides a surprising boost in the skin-conditioning efficacy of the sanitizing composition, while not deleteriously affecting the sanitizing efficacy, and also while providing good aesthetic qualities. Thus, in one or more embodiments, compositions of the present invention include at least one phytochemical with anti-inflammatory properties and at least one enzyme or coenzyme that aids in the formation of skin stratum corneum.

a. Phytochemicals with Anti-Inflammatory Properties

In one or more embodiments, at least one of the primary skin-conditioning agents includes a phytochemical having anti-inflammatory properties. Advantageously, in one or more embodiments the phytochemical also has anti-oxidant properties.

Examples of phytochemicals having anti-inflammatory properties include avenanthramides, trehalose, Boswellic acids-mixture of penta and tetracycline triterpene acids, Leukotrienes, Cochichine, *Verbene officinalis*, Willow-bark extract, *Aloe* species, *Arnica montana* extract, *Symphytum officianele, Calendula officinalis, Hamamelis virginiana, Quercus* cortex, Capsaicin (*Capsicum annuum* L.), Salicin, *Selenium*, Chamomile Extract, Licorice extract, Alpine lichen, *Rooibos* extract, Wheat protein hydrolysate, Bentonite, Sea Mayweed-*Tripleurospermum maritimum* extract, Caprylic/Capric Triglyceride—*Beta vulgaris* (beet) root extract, Butylene glycol—*Aster maritime/Tripolium* extract, *Eryngium maritimum* callus culture filtrate, Algae Extract and Mugwort (*Artemisia vulgaris*) Extract, Hydrolyzed Algin, *Opuntia ficus-indica* (Napol Cactus) Fruit Extract, Dipotassium Glycyrrhizinate (extracted from licorice roots), Stearyl Glycyrrhetinate (extracted from licorice roots), *Calophyllum Inophyllum* Seed Oil, and *Evodia rutaecarpa* Fruit Extract and Butyl Glycol and Butylated Hydroxytoluene, and combinations thereof. In one or more embodiments, the at least one phytochemical includes an avenanthramide. In one or more embodiments, the at least one phytochemical includes trehalose.

Avenanthramides are a type of oat phytoalexins that exist predominantly in the groats of oat seeds. Generally, avenanthramides include an anthranilic acid derivative linked to a hydroxycinnamic acid derivative with a pseudo peptide bond. Avenanthramides are sometimes referred to as hydroxycinnamoyl alkaloids. Examples of avenanthramides include Bc (also called avenanthramide C), Bf (also called avenanthramide B) and Bp (also called avenanthramide A).

Avenanthramides are found in the extract of oat kernels. Oat kernel extracts are sometimes referred to as *Avena sativa* kernel extract. Commercially available products include those designated by the International Nomenclature for Cosmetic Ingredients (INCI) as *Avena Sativa* (Oat) Extract. for example from Ceapro Inc., under the tradename CP Oat Avenanthramides, which is said to contain 100-120 ppm avenanthramides AF-1, AF-2, and AF-6 in glycerin, with 0.2 wt. % potassium sorbate as a preservative.

In one or more embodiments, the avenanthramides may be represented by the following chemical structure:

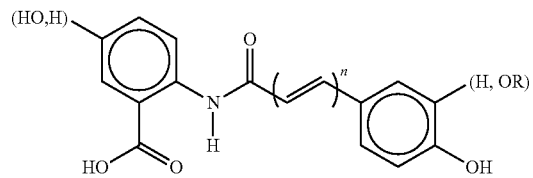

In one or more embodiments, the composition includes at least one phytochemical having anti-inflammatory properties in an amount of at least about 0.001 parts per million by weight (ppm), in other embodiments, at least about 0.002 ppm, in other embodiments, at least about 0.005 ppm, in other embodiments, at least about 0.01 ppm, in other embodiments, at least about 0.02 ppm, in other embodiments, at least about 0.05 ppm, in other embodiments, at least about 0.1 ppm, based upon the total weight of the composition.

In one or more embodiments, the composition includes at least one phytochemical having anti-inflammatory properties in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, based upon the total weight of the composition.

In one or more embodiments, the composition includes at least one phytochemical having anti-inflammatory properties in an amount of from about 0.001 ppm to about 10 wt. %, in other embodiments, from about 0.005 ppm to about 8 wt. %, and in other embodiments, from about 0.01 to about 5 wt. %, based upon the total weight of the composition.

Advantageously, as a result of the surprising synergistic effect of the combination of primary skin-conditioning agents, beneficial skin-conditioning effects are achieved with compositions containing relatively low amounts of primary skin-conditioning agents. In one or more embodiments, the composition includes at least one phytochemical having anti-inflammatory properties, in an amount of up to about 10 ppm, in other embodiments, up to about 8 ppm, in other embodiments, up to about 5 ppm, in other embodiments, up to about 3 ppm, in other embodiments, up to about 1 ppm, in other embodiments, up to about 0.5 ppm, in other embodiments, up to about 0.3 ppm, in other embodiments, up to about 0.1 ppm, based upon the total weight of the composition.

In one or more embodiments, the composition includes trehalose in an amount of at least about 0.001 parts per million by weight (ppm), in other embodiments, at least about 0.002 ppm, in other embodiments, at least about 0.005 ppm, in other embodiments, at least about 0.01 ppm, in other embodiments, at least about 0.02 ppm, in other embodiments, at least about 0.05 ppm, in other embodiments, at least about 0.1 ppm, based upon the total weight of the composition.

In one or more embodiments, the composition includes trehalose in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, based upon the total weight of the composition.

In one or more embodiments, the composition includes trehalose in an amount of from about 0.001 ppm to about 10 wt. %, in other embodiments, from about 0.005 ppm to about 8 wt. %, and in other embodiments, from about 0.01 to about 5 wt. %, based upon the total weight of the composition.

In one or more embodiments, the composition includes at least one avenanthramide having anti-inflammatory properties in an amount of at least about 0.001 parts per million by weight (ppm), in other embodiments, at least about 0.002 ppm, in other embodiments, at least about 0.005 ppm, in other embodiments, at least about 0.01 ppm, in other embodiments, at least about 0.02 ppm, in other embodiments, at least about 0.05 ppm, in other embodiments, at least about 0.1 ppm, based upon the total weight of the composition.

In one or more embodiments, the composition includes at least one avenanthramide having anti-inflammatory properties in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, based upon the total weight of the composition.

In one or more embodiments, the composition includes at least one avenanthramide having anti-inflammatory properties in an amount of from about 0.001 ppm to about 10 wt. %, in other embodiments, from about 0.005 ppm to about 8 wt. %, and in other embodiments, from about 0.01 ppm to about 5 wt. %, based upon the total weight of the composition.

As a result of the surprising synergistic effect of the combination of avenanthramide with another skin-conditioning agent such as niacinamide, beneficial skin-conditioning effects are achieved with compositions containing relatively low amounts of avenanthramide. In one or more embodiments, the composition includes at least one avenanthramide in an amount of up to about 10 ppm, in other embodiments, up to about 8 ppm, in other embodiments, up to about 5 ppm, in other embodiments, up to about 3 ppm, in other embodiments, up to about 1 ppm, in other embodiments, up to about 0.5 ppm, in other embodiments, up to about 0.3 ppm, in other embodiments, up to about 0.1 ppm, based upon the total weight of the composition.

In one or more embodiments, the amount of avenanthramides is from about 0.001 to about 0.5 ppm, in other embodiments, from about 0.002 to about 0.3, and in other embodiments, from about 0.003 to about 0.1 ppm, based upon the total weight of the composition.

In one or more embodiments, the phytochemical may be added to the composition as a solution or emulsion. In other words, the phytochemical may be premixed with a carrier to form a phytochemical solution or emulsion, with the proviso that the carrier does not deleteriously affect the sanitizing properties or conditioning properties of the composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the phytochemical is premixed to form a phytochemical solution or emulsion, the amount of solution or emulsion that is added to the composition is selected so that the amount of phytochemical falls within the ranges set forth hereinabove.

b. Stratum Corneum Formation Enhancer

In one or more embodiments, at least one of the primary skin-conditioning agents includes an enzyme or coenzyme that aids in the formation of the stratum corneum. Advantageously, the enzyme or coenzyme that aids in the formation of the stratum corneum enhances barrier repair. In one or more embodiments, the stratum corneum formation enhancer also aids in lipid regulation.

In one or more embodiments, the composition includes at least one stratum corneum formation enhancer selected from the group consisting of vitamin B, such as vitamin B3 or vitamin B complex, retinol, retinaldehyde, retinoic acid, epigallocatechin-3-gallate, eicosapentaenoic acid, hexamidine, niacinamide, lecithin, linolenic acid, linolenic acid, lipoic acid, lysstine, phospholipids, carnitine, carnosine, adenosine triphosphate, adenosine cyclic phosphate, palmitoyl oligopeptide, palmitoyl tripeptide-3 (and most other peptides), and *pyrus malus* (apple) fruit extract. In one or more embodiments, the stratum corneum formation enhancer is vitamin B3, which is sometimes referred to as niacinamide or niacin.

In one or more embodiments, the composition includes at least one enzyme or coenzyme that aids in the formation of the stratum corneum in an amount of at least about 0.0005 wt. %, in other embodiments, 0.001 wt. %, in other embodiments, at least about 0.002 wt. %, in other embodiments, at least about 0.005 wt. %, in other embodiments, at least about 0.01 wt. %, in other embodiments, at least about 0.02 wt. %, in other embodiments, at least about 0.05 wt. %, in other embodiments, at least about 0.1 wt. %, based upon the total weight of the composition.

In one or more embodiments, the composition includes at least one enzyme or coenzyme that aids in the formation of the stratum corneum in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, in other embodiments, up to about 0.3 wt. %, in other embodiments, up to about 0.1 wt. %, in other embodiments, up to about 0.05 wt. %, based upon the total weight of the composition.

In one or more embodiments, the composition includes at least one enzyme or coenzyme that aids in the formation of the stratum corneum in an amount of from about 0.001 to about 10 wt. %, in other embodiments, from about 0.005 to about 8 wt. %, and in other embodiments, from about 0.01 to about 5 wt. %, based upon the total weight of the composition.

In one or more embodiments, the composition includes niacinamide in an amount of at least about 0.001 wt. %, in other embodiments, at least about 0.002 wt. %, in other embodiments, at least about 0.005 wt. %, in other embodiments, at least about 0.01 wt. %, in other embodiments, at least about 0.02 wt. %, in other embodiments, at least about 0.05 wt. %, based upon the total weight of the composition.

In one or more embodiments, the composition includes niacinamide in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, in other embodiments, up to about 0.3 wt. %, in other embodiments, up to about 0.1 wt. %, in other embodiments, up to about 0.05 wt. %, based upon the total weight of the composition.

In one or more embodiments, the composition includes niacinamide in an amount of from about 0.001 to about 10 wt. %, in other embodiments, from about 0.005 to about 8 wt. %, and in other embodiments, from about 0.01 to about 5 wt. %, based upon the total weight of the composition.

In one or more embodiments, the amount of niacinamide is from about 0.01 to about 10 wt. %, in other embodiments, from about 0.05 to about 5, and in other embodiments, from about 0.1 to about 1 wt. %, based upon the total weight of the composition.

Advantageously, as a result of the surprising synergistic effect of the combination of primary skin-conditioning agents, beneficial skin-conditioning effects are achieved with compositions containing relatively low amounts of the stratum corneum formation enhancer. For example, in one or more embodiments, the composition includes niacinamide in an amount of up to about 0.5 wt. %, in other embodiments, up to about 0.3 wt. %, in other embodiments, up to about 0.1 wt. %, in other embodiments, up to about 0.05 wt. %, based upon the total weight of the composition.

In one or more embodiments, the total amount of primary skin conditioning agents that is present in the composition is less than about 1 wt. %, in other embodiments, less than about 0.8 wt. %, in other embodiments, less than about 0.5 wt. %, in other embodiments, less than about 0.4 wt. %, in other embodiments, less than about 0.3 wt. %, based upon the total weight of the composition.

IV. Deposition Enhancer

In one or more embodiments, the compositions of the invention include at least one deposition enhancer. Advantageously, the deposition enhancer is non-toxic, non-irritating and non-allergenic. Suitable deposition enhancers work rapidly with predictable and reproducible activity and duration. Suitably, the deposition enhancer has no significant pharmacological activity within the body, and when removed from the skin, barrier properties return rapidly and fully to normal. The deposition enhancer primarily works unidirectionally, i.e., allows therapeutic agents into the body whilst preventing the loss of endogenous materials from the body. Advantageously, the deposition enhancer provides a cosmetically acceptable appearance and an acceptable skin feel.

In one or more embodiments, examples of deposition enhancers include surfactants, bile salts and derivatives thereof, fatty acids and derivatives thereof, chelating agents, and sulphoxides.

Examples of deposition enhancers include dimethyl sulphoxides (DMSO), DMA, DMF, 1-dodecylazacycloheptan-2-one (azone), pyrrolidones such as 2-Pyrrolidone (2P) and N-Methyl-2-Pyrrolidone (NMP), long-chain fatty acids such as oleic acid and fatty acids with a saturated alkyl chain length of about $C_{10}$-$C_{12}$, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, lecithin.

In one or more embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer.

In one or more embodiments, the composition includes a deposition enhancer in an amount of up to about 10 weight percent (wt. %), in other embodiments, up to about 8 wt. %, in other embodiments, up to about 5 wt. %, in other embodiments, up to about 3 wt. %, in other embodiments, up to about 1 wt. %, in other embodiments, up to about 0.5 wt. %, in other embodiments, up to about 0.3 wt. %, in other embodiments, up to about 0.1 wt. %, in other embodiments, up to about 0.05 wt. %, based upon the total weight of the composition.

In one or more embodiments, the composition includes a deposition enhancer in an amount of at least about 0.005 wt. %, in other embodiments, 0.01 wt. %, in other embodiments, at least about 0.02 wt. %, in other embodiments, at least about 0.05 wt. %, in other embodiments, at least about 0.1 wt. %, in other embodiments, at least about 0.2 wt. %, in other embodiments, based upon the total weight of the composition.

In one or more embodiments, the amount of deposition enhancer is from about 0.005 to about 10 wt. %, in other embodiments, from about 0.01 to about 5, and in other embodiments, from about 0.05 to about 3 wt. %, based upon the total weight of the composition.

In one or more embodiments, the amount of hydroxy-terminated polyurethane compound is from about 0.005 to about 5, in other embodiments, from about 0.01 to about 3, and in other embodiments, from about 0.05 to about 1 wt. %, based upon the total weight of the composition.

V. Optional Ingredients

The compositions of the present invention can further comprise a wide range of optional ingredients, with the proviso that they do not deleteriously affect the sanitizing efficacy of the compositions, the aesthetics of the compositions, or the skin-conditioning properties of the compositions. With respect to sanitizing efficacy, deleterious should be interpreted to mean that the decrease in the $\log_{10}$ reduction according to established antimicrobial efficacy tests, or in other words, the log reduction does not decrease by more than about 0.5.

The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anti-caking agents, antioxidants such as guiazulene and spirulina, antipruritics, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials that may be useful herein include solubilizing agents, sequestrants, keratolytics, topical active ingredients, and the like.

a. Humectants

In certain embodiments, the composition comprises one or more humectants. Examples of humectants include propylene glycol, hexylene glycol, 1,4-dihydroxyhexane, 1,2, 6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, hydroxyethyl urea, alpha-hydroxy acids, such as lactic acid, sodium pyrrolidone carboxylic acid, hyaluronic acid, chitin, and the like.

Examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

In one or more embodiments, the composition includes at least one humectant in an amount of at least about 0.001 wt. %, in other embodiments, at least about 0.002 wt. %, in other embodiments, at least about 0.005 wt. %, in other embodiments, at least about 0.01 wt. %, in other embodiments, at least about 0.02 wt. %, in other embodiments, at least about 0.05 wt. %, in other embodiments, at least about 0.1 wt. %, in other embodiments, at least about 0.2 wt. %, in other embodiments, at least about 0.5 wt. %, in other embodiments, at least about 0.7 wt. %, in other embodiments, at least about 1 wt. %, in other embodiments, at least about 1.5 wt. %, in other embodiments, at least about 2 wt. %, based upon the total weight of the composition.

In one or more embodiments, the composition includes at least one humectant in an amount of up to about 20 wt. %, in other embodiments, up to about 15 wt. %, in other embodiments, up to about 10 wt. %, in other embodiments, up to about 8 wt. %, in other embodiments, up to about 5 wt. %, in other embodiments, up to about 3 wt. %, based upon the total weight of the composition.

Advantageously, as a result of the surprising synergistic effect of the combination of primary skin-conditioning agents, beneficial skin-conditioning effects are achieved with compositions containing relatively low amounts of humectants. In one or more embodiments, the total amount of humectants in the composition may be less than about 2 wt. %, in other embodiments, less than about 1 wt. %, in other embodiments, less than about 0.5 wt. %, in other embodiments, less than about 0.1 wt. %, based upon the total weight of the composition. In one or more embodiments, the amount of glycerin may be less than about 2 wt. %, in other embodiments, less than about 1 wt. %, in other embodiments, less than about 0.5 wt. %, in other embodiments, less than about 0.1 wt. %, based upon the total weight of the composition. It is believed that one of the reasons that compositions of the present invention have better aesthetics is due to the lower amount of total raw materials that are required to produce a product with effective skin-conditioning benefits.

b. Moisturizing Esters

In these or other embodiments, the composition comprises one or more conditioning or moisturizing esters. Examples of esters include cetyl myristate, cetyl myristoleate, and other cetyl esters, diisopropyl sebacate, and isopropyl myristate.

In one or more embodiments, the composition includes at least one conditioning or moisturizing ester in an amount of up to about 10% by weight, in other embodiments, up to about 5 wt. %, in other embodiments, up to about 2 wt. %, in other embodiments, up to about 1 wt. %, based upon the total weight of the composition.

In one or more embodiments, the composition includes at least one conditioning or moisturizing ester in an amount of at least about 0.001 wt. %, in other embodiments, at least about 0.002 wt. %, in other embodiments, at least about 0.005 wt. %, in other embodiments, at least about 0.01 wt. %, in other embodiments, at least about 0.02 wt. %, in other embodiments, at least about 0.05 wt. %, in other embodiments, at least about 0.1 wt. %, in other embodiments, at least about 0.2 wt. %, in other embodiments, at least about 0.5 wt. %, in other embodiments, at least about 0.7 wt. %, in other embodiments, at least about 1 wt. %, based upon the total weight of the composition.

In another embodiment each ester that is included is present in an amount of from about 0.5 to about 5% by weight, in another embodiment from about 1 to about 2% by weight, based upon the total weight of the composition.

On the other hand, as a result of the surprising synergistic effect of the combination of primary skin-conditioning agents, moisturizing esters are not required, or may be present in relatively low amounts. In one or more embodiments, the total amount of moisturizing esters in the composition may be less than about 1 wt. %, in other embodiments, less than about 0.5 wt. %, in other embodiments, less than about 0.1 wt. %, in other embodiments, less than about 0.05 wt. %, based upon the total weight of the composition.

c. Emulsifying Agents

In one or more embodiments, the composition may include one or more emulsifying agents. Examples of emulsifying agents include stearyl alcohol, sorbitan oleate trideceth-2, poloxamers, and PEG/PPG-20/6 dimethicone. In one embodiment, the emulsifying agent is present in an amount of up to about 10% by weight, based upon the total weight of the antimicrobial composition. In another embodiment the emulsifying agent is present in an amount of from about 0.1 to about 5% by weight, in another embodiment from about 0.5 to about 2% by weight, based upon the total weight of the antimicrobial composition.

d. Silicone Glycols

In one or more embodiments, the composition includes one or more silicone glycols. Silicone glycols may be generally characterized by containing one or more Si—O—Si linkages in the polymer backbone. Silicone glycols include organopolysiloxane dimethicone polyols, silicone carbinol fluids, silicone polyethers, alkylmethyl siloxanes, amodimethicones, trisiloxane ethoxylates, dimethiconols, quaternized silicone glycols, polysilicones, silicone crosspolymers, and silicone waxes.

Examples of silicone glycols include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG 23/PPG 6 dimethicone, PEG 20/PPG 23 dimethicone, PEG 17 dimethicone, PEG5/PPG3 methicone, bis PEG20 dimethicone, PEG/PPG20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

In one embodiment, the silicone glycol includes a compound that may be represented by the formula

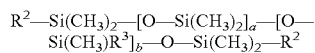

where $R^2$ and $R^3$ independently include a methyl group or a moiety that may be represented by the formula

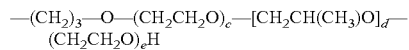

with the proviso that both $R^2$ and $R^3$ are not $CH_3$, where a is an integer from about 3 to about 21, b is an integer from about 1 to about 7, c is an integer from about 0 to about 40, d is an integer from about 0 to about 40, and e is an integer from about 0 to about 40, with the proviso that a ≥3×b and that c+d+e≥5.

In one or more embodiments, the composition includes at least about 0.002 wt. % of silicone glycol, based upon the total weight of the composition. In another embodiment, the composition includes at least about 0.01 wt. % of silicone glycol, based upon the total weight of the composition. In yet another embodiment, the composition includes at least about 0.05 wt. % of silicone glycol, based upon the total weight of the composition.

In one embodiment, each silicone glycol that is present in the composition is present in an amount of from about 0.002 to about 4 weight percent, based upon the total weight of the composition, although higher amounts may also be useful. In another embodiment, each silicone glycol is optionally present in an amount of from about 0.01 to about 2 weight percent, based upon the total weight of the composition. All such weights as they pertain to listed ingredients are based on the active level and, therefore, do not include carriers or by-products that may be included in commercially available materials, unless otherwise specified.

In one or more embodiments, the silicone glycol is selected from PEG-12 dimethicone, PEG-10 dimethicone, PEG-8 dimethicone, and combinations thereof.

e. Miscellaneous Skin-Conditioners

In one or more embodiments, the composition includes one or more miscellaneous skin-conditioners selected from *aloe*, vitamin E, and $C_{6-10}$ alkane diols.

In one or more embodiments, the composition may further comprise one or more $C_{6-10}$ alkane diols, i.e. diols having a carbon chain length of 6 to 10. In one or more embodiments, the diol comprises a straight chain diol. In one or more embodiments, the diol includes 1,2-hexanediol, 1,2-octanediol, 1,9-nonanediol, 1,2-decanediol, 1,10-decanediol, or a mixture thereof. 1,2-octanediol is sometimes referred to as caprylyl glycol. In one or more embodiments, the diol comprises one or more $C_{6-8}$ alkane diols, i.e. diols having a carbon chain length of 6 to 8.

In one or more embodiments, the composition includes a $C_{6-10}$ alkane diol in an amount of from about 0.05 to about 4 wt. %, based upon the total weight of the composition. In one embodiment, the diol is present in an amount of from about 0.1 to about 1 wt. %, in another embodiment, the diol is present in an amount of from about 0.15 to about 0.7 wt. %, in yet another embodiment, from about 0.2 to about 0.6 wt. %, and in still yet another embodiment, from about 0.25 to about 0.5 wt. %, based upon the total weight of the composition. It will be understood that greater amounts of diol can be employed, if desired, and are expected to perform at least equally as well.

It should be understood that emollients, humectants, moisturizing esters, and other skin-conditioning agents are not required in the compositions of the present invention, and can be limited, if desired, for example to achieve improved aesthetics and/or to avoid deleterious effects on antimicrobial efficacy. That is, compositions of the present invention containing a $C_{1-6}$ alcohol, primary skin conditioning agents as described above, and a deposition enhancer may contain no additional skin conditioning agents, or may contain additional skin conditioning agents in only limited amounts, i.e. amounts that are significantly lower than what is found in other alcoholic products that claim skin conditioning benefits. Thus, for purposes of this specification, the term "additional skin conditioning agents" may be defined as any emollients, humectants, moisturizing agents, occlusive agents and the like that are not phytochemicals having anti-inflammatory properties and enzymes or coenzymes that aid in the formation of the skin stratum corneum.

In one or more embodiments, the total amount of additional skin conditioning agents in the composition may be less than about 2 wt. %, in other embodiments, less than about 1.5 wt. % in other embodiments, less than about 1 wt. %, in other embodiments, less than about 0.75 wt. %, in other embodiments, less than about 0.5 wt. %, based upon the total weight of the composition. In other embodiments, the compositions of the present invention are devoid of additional skin conditioning agents.

f. Thickeners

In one or more embodiments, the compositions of the present invention may be thickened. Advantageously, a thickener system may be employed that is compatible with the alcoholic compositions described above, in order to provide suitable stability, acceptable cosmetic properties, and appropriate viscosity.

In one or more embodiments, compositions of this invention have a viscosity of at least about 100 centipoise (cps), in other embodiments, at least about 500, in other embodiments, at least about 1,000, in other embodiments, at least about 1,500, in other embodiments, at least about 2,000, in other embodiments, at least about 3,000, in other embodiments, at least about 4,000, in other embodiments, at least about 10,000 cps, in other embodiments, at least about 20,000 cps, in other embodiments, at least about 50,000 cps, and in other embodiments, at least about 80,000 cps, at 23° C., measured using a suitable viscometer and spindles. For example, in one or more embodiments, the viscosity may be measured using a very low shear viscometer such as Brookfield LVDV-I+ viscometer and T spindles with a heliopath adapter. Unless stated otherwise, the measured viscosity is that of the final composition.

In one or more embodiments, compositions of the present invention may be thickened by using thickener systems based upon non-ionic and/or cationic surfactants, as further described in U.S. Pat. No. 8,062,649, which is hereby incorporated by reference.

In one or more embodiments, the non-ionic and/or cationic surfactant-based thickener system is present in an amount of from about 0.5 to about 10 wt. %, in other embodiments, from about 1 to about 8 wt. %, and in other embodiments, from about 2 to about 6 wt. %, based upon the total weight of the composition.

As used herein, a polymeric thickener is considered part of the thickener system if it is nonionic or cationic and its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than about 20,000) do not increase the viscosity of the composition significantly. These may be considered as emollients or humectants.

In one or more embodiments, the polymeric thickener system includes at least one cationic or nonionic polymer that is solid at ambient temperature. Examples of cationic polymeric thickeners include cationically modified celluloses, quaternized natural amino-functional polymers, and polymers based on ethylenically unsaturated monomers selected from the group of acrylates, acrylamides, vinyl lactams, vinyl acetates, methyl vinyl ethers, styrene, and acrylonitrile. Examples of nonionic polymeric thickeners include modified celluloses, associative polymers based on nonionic ethylenically unsaturated monomers wherein at least one comonomer has at least 16 carbon atoms, and polymers based on ethylenically unsaturated monomers selected from the group of acrylates, acrylamides, vinyl lactams, vinyl acetate and its hydrolyzed derivatives, methyl vinyl ethers, styrene, and acrylonitrile.

Further examples include cationic modified cellulosic polymers that are soluble in water, such as modified cellulose products sold under the trade names "CELQUAT" (National Starch and Chemicals Corp., Bridgewater, N.J.) and "UCARE" (Amerchol Corporation, Edison, N.J.). "CELQUAT" is a copolymer of a polyethoxylated cellulose and dimethyldiallyl ammonium chloride and has the Cosmetic, Toiletry and Fragrance Association (CTFA) designation Polyquaternium-4. Examples of "CELQUAT" polymers are "CELQUAT" SC-230M and H-100. "UCARE" is a polymeric quaternary ammonium salt of hydroxyethylcellulose and a trimethyl ammonium chloride substituted epoxide and has the CTFA designation Polyquaternium-10. Examples of "UCARE" polymers include "UCARE" JR-30M.

An alkyl modified quaternary ammonium salt of hydroxyethyl cellulose and a trimethyl ammonium chloride substituted epoxide has also been found to be useful. The polymer conforms to the CTFA designation Polyquaternium 24 and is commercially available as "QUATRISOFT" LM-200 from Amerchol Corp., Edison, N.J.

Examples of cationic synthetic polymers useful in the present invention include homopolymers that are comprised of one of the following monomers: methacryloyloxyalkyl trialkyl ammonium salt, acryloyloxyalkyl trialkyl ammonium salt, and quaternized dialkylaminoalkylacrylamidine salt, and copolymers comprised of at least two monomers selected from the group: trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, and acrylonitrile. Typically, for the salts the counterions include $F^-$, $Cl^-$, $Br^-$, and $CH_3(CH_2)_n$—$SO_4^-$ where n=0-4.

A variety of quaternary copolymers of varying quaternization, can be synthesized based on homo or copolymers of amino acrylates with methyl, ethyl or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with water-soluble monomers, such as Petrolite Product No. Q-0043, a proprietary copolymer of a linear quaternary acrylate and acrylamide at high molecular weight (4-5 million MW).

Examples of cationic polymers include N,N-dimethylaminopropyl-N-acrylamidine quaternized with diethylsulfate and bound to a block of polyacrylonitrile. This block copolymer is available as "Hypan QT-100" from Lipo Chemicals Inc., Paterson, N.J. Further examples include ammonium acryloyldimethyltaurate/VP copolymer, available from Clariant under the tradename Aristoflex® AVC.

Examples of suitable nonionic polymers include methylhydroxypropylcellulose, available as "BENECEL MP 943" from Aqualon, Wilmington, Del.; hydroxypropylcellulose, available as "KLUCEL" (LF, GF, MF, HF) from Aqualon, Wilmington, Del.; and hydroxybutylmethylcellulose (3.5% hydroxybutyl and 30% methoxyl) from Scientific Polymer Products, Ontario, N.Y.

Examples of suitable swellable polymers include crosslinked polymers polymers of acrylamide and at least one other quaternary monomer selected from the group of trialkylaminoalkylacrylate and methacrylate salts, dialkyldiallyl ammonium salts, acrylamidoalkyltrialkyl ammonium salts, methacrylamidoalkyltrialkyl ammonium salts, and monomers comprising imidazolinium salts. The counterions are preferably $F^-$, $Cl^-$, $Br^-$, and $CH_3(CH_2)_n$—$SO_4^-$ where n=0-4. Other comonomers may also be added including N-vinyl pyrrolidone, N-vinyl caprolactam, methyl vinyl ether, acrylates, methacrylates, styrene, and the like. In one or more embodiments, the polymer is comprised of a poly(2-methacryloxyethyl trimethyl ammonium chloride) polydimethylaminoethyl methacrylate, which conforms to the CTFA designation Polyquaternium 37. In one or more embodiments, the polymer is comprised of acrylamide and methacryloyloxyethyl trimethyl ammonium chloride, which conforms to the CTFA designation Polyquaternium 32. These are commercially available from Allied Colloids Inc. of Suffolk, Va. as "SALCARE" SC95, SC96, and SC92.

Other swellable polymers (i.e., slightly crosslinked polymers) can be prepared using ionizing radiation to crosslink. For examples, polymers comprising N-vinyl lactams, such as N-vinyl pyrrolidone, "LUVIQUAT HM 552" (copolymers of vinylimidazolium methochloride and vinylpyrrolidone, which conforms to the CTFA designation Polyquaternium-16), and "GAFQUAT HS-100" (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups as used herein include substituted derivatives. Exemplary compounds include divinyl, diallyl, or dimethallyl esters, ethers, amides, or ureas. Specific examples are disclosed in U.S. Pat. Nos. 5,225,473 and 4,931,282. Further examples include crosslinked polyvinylpyrrolidone (PVP) materials prepared via covalent crosslinking with diallyl maleate or by radiation crosslinking of linear PVP powders.

Examples of associate polymers include polymers that are based on nonionic ethylenically unsaturated monomers wherein at least one comonomer has at least 16 carbon atoms. An example is cetyl hydroxyethylcellulose, available as "NATROSOL PLUS" from Aqualons.

In one or more embodiments, compositions of the present invention may be thickened by using thickener systems based upon emulsifiers, as further described in U.S. Pat. No. 7,803,390, which is hereby incorporated by reference.

Examples of thickeners also include polysaccharaide thickeners, such as starch, vegetable gums, pectin, and guar.

In one or more embodiments, the compositions of the present invention may be thickened with a polyacrylate thickener. Examples of polyacrylate thickeners include carbomers, acrylates/C10-30 alkyl acrylate crosspolymers, copolymers of acrylic acid and alkyl(C5-C10) acrylate, copolymers of acrylic acid and maleic anhydride, and mixtures thereof.

In one or more embodiments, the polymeric thickener includes from about 0.5% to about 4% by weight of a cross-linking agent. Examples of cross-linking agents include the polyalkenyl polyethers.

Commercially available polymers of the polyacrylate type include those sold under the trade names Carbopol®, Acrysol® ICS-1, Polygel®, Sokalan®, Carbopol® 1623, Carbopol® 695, Ultrez 10, and Polygel® DB.

In one or more embodiments, the amount of thickener is at least about 0.01 wt. %, based upon the total weight of the composition, in other embodiments, at least about 0.02 wt. %, in yet other embodiments at least about 0.05 wt. %, and it still other embodiments, at least about 0.1 wt. %, based upon the total weight of the composition. In one or more embodiments, the thickener is present in an amount of at least about 0.5 wt. %, and in other embodiments, at least about 0.75 wt. %, based upon the total weight of the composition. In one or more embodiments, the compositions according to the present invention comprise up to about 10% by weight of the total composition of a polymeric thickener. In one or more embodiments, the amount of thickener is from about 0.01 to about 1 wt. %, in other embodiments, from about 0.02 to about 0.4 wt. %, and in other embodiments, from about 0.05 to about 0.3 wt. %, based upon the total weight of the composition. In one or more embodiments, the amount of thickener is from about 0.1 to about 10 wt. %, in other embodiments from about 0.5% to about 5% by weight, in other embodiments from about 0.75% to about 2% wt. %, based upon the total weight of the composition.

In one or more embodiments, the composition may further comprise a neutralizer. The use of neutralizing agents to form salts of carbomer polymers is known. Examples of neutralizing agents include amines, alkanolamines, alkanolamides, inorganic bases, amino acids, including salts, esters and acyl derivatives thereof.

In one or more embodiments, the composition may be formulated as a hydroalcoholic gel that may be characterized by a viscosity range of from about 5,000 to about 80,000 cps, in other embodiments, from about 5000 to about 35,000 cps, and in other embodiments, from about 10,000 to about 25,000 cps. In one or more embodiments, the viscosity may be measured by a Brookfield RV Viscometer using RV and/or LV Spindles at 22° C.+/−3° C. Hydroalcoholic gels are further described in U.S. Pub. Pat. Appl. No. 2010/0317743 A1 (P285), which is hereby incorporated by reference.

g. Auxiliary Antimicrobial Agents

Any antimicrobial ingredient other than the $C_{1-6}$ alcohol may be referred to as an auxiliary antimicrobial agent. In one embodiment, the amount of auxiliary antimicrobial agent (including preservatives) is less than about 0.1 wt. %, in another embodiment, less than about 0.05 wt. %, based upon the total weight of the composition. In another embodiment, the composition is devoid of auxiliary antimicrobial agents.

It is envisioned that, in other embodiments, auxiliary antimicrobial agents could be included, with the proviso that the antimicrobial ingredient does not deleteriously affect the sanitizing properties of the composition. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecane-diimidi amide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, and mixtures thereof. In one or more embodiments, the auxiliary antimicrobial agents are present in amounts of from about 0.001 to about 2 wt. % each, based upon the total weight of the composition.

h. Limited Ingredients

Advantageously, certain ingredients that have been designated as critical to current antiseptic compositions can be limited in the composition of the present invention. For example, zinc compounds such as organic salts of zinc, zinc gluconate, zinc pyrithione, or zinc omadine are not necessary, and can be limited, if desired, to less than about 0.5 wt. %, or in another embodiment to less than about 0.1 wt. %, or in another embodiment to less than about 0.05 wt. %, based upon the total weight of the composition. In another embodiment, the composition is devoid of organic salts of zinc.

In one or more embodiments, the amount of acid may be limited. More specifically, in one or more embodiments, the amount of organic acid may be limited. In one or more embodiments, the amount of any of the following acids may be limited: citric acid, glycolic acid, lactic acid, malic acid, tartaric acid, and acetic acid. When limited, in one or more embodiments, the amount of acid may be less than 0.125 wt. %, in other embodiments less than about 0.08 wt. %, based upon the total weight of the composition. In another embodiment, the composition is devoid of citric acid, glycolic acid, lactic acid, malic acid, tartaric acid, and acetic acid.

In one or more embodiments, the amount of essential oil is less than 0.1 wt. %, or in another embodiment less than about 0.05 wt. %, based upon the total weight of the composition. In another embodiment, the composition is devoid of essential oils. More specifically, in one embodiment, the composition contains less than 0.1 wt. %, in another embodiment less than 0.05, and in another embodiment, is devoid of any of the following essential oils: cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, *eucalyptus* oil, lemon oil, orange oil, sweet orange oil, and *calendula* oil, wherein the above amounts are based upon the total weight of the composition.

In one or more embodiments, the amount of specific constituents of essential oils is also limited. More specifically, in one embodiment, the composition contains less than 0.1 wt. %, in another embodiment less than 0.05, and in another embodiment, is devoid of any of the following constituents of essential oils: farnesol, nerolidol, bisabolol, apritone, chamazulene, santalol, zingiberol, carotol, and caryophyllen, curcumin, 1-citronellol, α-amylcinnarnaldehyde, lyral, geraniol, farnesol, hydroxycitronellal, isoeugenol, eugenol, camphor, eucalyptol, linalool, citral, thymol, limonene and menthol, wherein the above amounts are based upon the total weight of the composition.

In one or more embodiments, the composition is devoid of traditional preservative agents, other than what may be present in trace amounts in one or more of the ingredients described hereinabove. For example, avenanthramides as commercially sold sometimes contain small amounts of preservative such as potassium sorbate. Traditional preservative agents include parabens, benzoic acid, potassium sorbate, iodopropynyl butylcarbomate, tropolone, dibromodicyanobutane, 1,2-benziosthiazolin-3-one, and phenoxyethanol. In one or more embodiments, the amount of preservative is less than about 1 wt. %, in other embodiments, less than about 0.5 wt. %, in yet other embodiments, less than about 0.1 wt. %, based upon the total weight of the composition.

Indeed, any component other than the alcohol, primary skin-conditioning agents, deposition enhancers, and water is not necessary and can optionally be limited to less than about 0.5 wt. %, if desired to less than about 0.1 wt. %, if desired to less than about 0.05 wt. %, if desired to less than about 0.01 wt. %, or if desired to less than about 0.001 wt. %.

i. Balance of Composition

In one or more embodiments, the balance of the composition includes water or other suitable solvent.

VI. Method of Mixing

The dispensable composition may be prepared by simply mixing the components together. The order of addition is not particularly limited, but may advantageously be selected based upon the solubility of various ingredients in water and/or alcohol.

VII. Misc. Characteristics of Composition

In one embodiment, where the composition is in liquid form, the percent solids of the composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

In one or more embodiments, the pH of the composition is from about 1.5 to about 10, in other embodiments from about 1.5 to about 4.5, in other embodiments from about 3 to about 4.5, in other embodiments from about 4.5 to about 9.5, in other embodiments from about 7 to about 8.

In one or more embodiments, the composition may be formulated as a non-aerosol foamable composition. In these or other embodiments, the composition may be characterized by a viscosity of less than about 100 cps, in other embodiments, less than about 50 cps, as measured by Brookfield RV Viscometer using RV and/or LV Spindles at 22° C.+/−3° C. Foamable compositions are further described in U.S. Pat. App. Publ. Nos. 2007/0148101 A1, 2012/0129950 A1, and 2015/0025156 A1, all of which are hereby incorporated by reference.

VIII. Five Moments for Hand Hygiene in Health Care

The World Health Organization (WHO) Guidelines on Hand Hygiene in Health Care formulated recommendations for hand hygiene for health care workers, and provided the chart shown in FIG. 1. Referring now to FIG. 1, it can been seen that five circumstances are identified under which it is recommended that a health care provided should perform hand hygiene. (1). Before touching a patient; (2). Before performing a clean/aseptic procedure; (3). After body fluid exposure risk; (4). After touching a patient; and (5). After touching patient surroundings.

IX. Advantages a. Reduced Irritancy and Improved Skin Moisture

Advantageously, embodiments of the present invention provide an effective healthcare personnel hand wash composition that maintains or improves skin hydration. By effective health care personnel hand wash composition is meant a composition that meets or exceeds the standards for health care personnel hand wash as set forth by the FDA Tentative Final Monograph for Healthcare Antiseptic Drug Products (TFM) (Federal Register 59 [116], Jun. 17, 1994: pp. 31402-31452) for healthcare personnel hand wash (the FDA TFM test for healthcare personnel hand wash). Compositions of the present invention have reduced irritancy when used according to current guidelines for hand hygiene for personnel in hospitals and health-care facilities, such as the WHO Guidelines on Hand Hygiene in Health Care. Furthermore, embodiments of the present invention have reduced irritancy when used in combination with typical hand washes. Embodiments of the present invention maintain skin condition, and do not dry out or damage the barrier function of skin, when used according to current guidelines for hand hygiene for personnel in hospitals and health-care facilities. Embodiments of the present invention actually improve skin condition, in terms of hydration, barrier function, and other parameters, when used according to current guidelines for hand hygiene for personnel in hospitals and health-care facilities.

Thus, the present invention provides methods for maintaining or improving skin condition of health care workers. The method includes providing a composition according to the present invention to a health care worker who uses the product to sanitize their hands according to the appropriate guidelines of the health care facility, or according to the WHO Guidelines On Hand Hygiene In Health Care shown in FIG. 1, over a period of time, and the skin condition of the user remains constant or improves. That is, when the skin condition of the health care worker's hands is measured prior to use of the product, and again after a period of use, the skin condition is at least as good, and in one or more embodiments is improved.

A healthcare worker who sanitizes his/her hands according to the appropriate guidelines may be referred to as a compliant worker. In some healthcare settings, a healthcare worker who sanitizes their hands according to the appropriate guidelines, i.e. a compliant worker, may use a sanitizer product to sanitizer his/her hands at least about 50 times during one work shift (8-12 hours), in some embodiments, at least about 80 times per shift, in other embodiments, at least 100 times per shift. In one or more embodiments, assuming that the compliant worker works 3-4 shifts per week, the skin condition on the hands of the compliant worker is maintained over a period of at least 3 days, in other embodiments, over a period of at least 7 days, in other embodiments, over a period of at least 14 days. In these embodiments, the hydration and/or the barrier function of the hand skin is at least as much after the period of use as the hydration and/or barrier function of the same skin prior to use.

In one or more embodiments, assuming that the compliant worker works 3-4 shifts per week, the skin condition on the hands of the compliant worker is improved over a period of at least 3 days. In these embodiments, the skin condition of the hand skin is improved after the period of use when compared to the skin condition of the same skin prior to use.

In some embodiments, improvement is seen within 7 days. In other embodiments, improvement is seen within 14 days.

Similarly, the present invention provides a method for improving skin condition of health care workers within 7 consecutive days, based upon daily use. The method includes providing a composition according to the present invention, applying the composition to the hands of the health care worker at least 50 times during a 24-hour day, and repeating the step of applying the composition to the hands of the health care worker on at least two additional 24-hour days within a total period of 7 consecutive days. In some embodiments, improvement is seen within 7 days. In other embodiments, improvement is seen within 14 days.

Embodiments of the present invention further provide a method for improving skin condition of health care workers within 3 days, the method comprising the steps of providing a composition according to any of the preceding claims, providing a health care worker with a need to sanitize their hands at least 50 times during a work shift, applying the composition to the hands of the health care worker at least 50 times during the work shift, wherein the health care worker works at least 3 shifts during 3 consecutive days.

Embodiments of the present invention further provide a method for improving skin condition of health care workers within 7 consecutive days, the method comprising the steps of providing a composition as described herein, applying the composition to the hands of the health care worker at least 50 times during a 24-hour day, and repeating the step of applying the composition to the hands of the health care worker on at least two additional 24-hour days within a total period of 7 consecutive days.

It has been seen that many persons who use conventional alcohol-based hand sanitizers at least 10 times per day experience a worsening of the skin condition of their hands over a period of 7 days or more. Advantageously, persons who use the alcohol-based hand sanitizers of the present invention at least 10 times per day over a 7 day period experience do not experience the same level of worsening of the skin condition of their hands, when compared to persons who use conventional alcohol-based hand sanitizers. In one or more embodiments, persons who use the alcohol-based hand sanitizers of the present invention at least 10 times per day over a 7 day period experience improvement in the skin condition of the hands.

In one or more embodiments, the improved skin condition includes reduced irritancy and/or improved skin moisture. In one or more embodiments, the improved skin condition may be expressed broadly in terms of irritancy and moisture/barrier function, or more specifically as redness, hydration, moisture loss, dryness through visual grading.

In one or more embodiments, skin condition may be measured by using a protocol that is sometimes referred to as the forearm controlled application technique (FCAT). The FCAT is described in Ertel, Keith D. et al., "A forearm controlled application technique for estimating the relative mildness of personal cleansing products," *J. Soc. Cosmet. Chem.*, 46, 67-76 (March/April 1995), which is hereby incorporated by reference. The method may be modified to test leave-on type products, such as alcoholic sanitizers that are rubbed in and/or evaporated and do not need to be rinsed off, as follows.

FCAT is actually a protocol for applying a product to skin—the skin can then be tested for various parameters/characteristics including broadly irritancy and moisture/barrier function—more specifically redness, hydration, moisture loss, dryness through visual grading, The test sites are washed and marked. One site may remain untreated. A control product may be used on one site Skin measurements may taken before any product is applied in order to establish a baseline. In one or more embodiments, skin hydration is measured using a corneometer and trans-epidermal water loss (TEWL) is measured by using an Aquaflux™ or VapoMeter™ closed chamber humidity meter.

Test product may be applied to one of the prepared sites, and another skin hydration measurement may be taken after a desired period of time. The process of applying product and measuring hydration may be repeated as desired. If desired, a step of washing the site with a handwash may be conducted at various intervals. A more irritating product will lead to a decline in skin hydration, and a less irritating product will not produce any change in skin hydration. A skin-conditioning product will lead to an increase in skin hydration.

In one or more embodiments, compositions of the present invention provide increased skin hydration.

b. Reduced Abnormal Desquamation

In one or more embodiments, the improved skin condition includes reduced abnormal, or pathologic, desquamation.

Advantageously, compositions of the present invention have reduced abnormal, or pathologic, desquamation when used according to current guidelines for hand hygiene for personnel in hospitals and health-care facilities. Embodiments of the present invention have reduced pathologic desquamation when used in combination with typical hand washes. Embodiments of the present invention actually improve skin condition, in terms of pathologic desquamation, when used according to current guidelines for hand hygiene for personnel in hospitals and health-care facilities.

In one or more embodiments, desquamation, including pathologic desquamation, may be measured by using D-Squame® skin analysis disks, available from CuDerm Corporation, at baseline, at 2 weeks, and at 4 weeks, and an improvement will be seen when the product is used according to current guidelines for hand hygiene for personnel in hospitals and health-care facilities. In one or more embodiments, a decrease in desquamation is seen when used by a health care worker at the "5 Moments of Hand Hygiene," over a period of 4 weeks, in other embodiments, over a period of 2 weeks, and in other embodiments, when the product is used daily, at least 50 times per day, over a period of 4 weeks, in other embodiments, over a period of 2 weeks, and in other embodiments, over a period of 1 week.

c. Aesthetics

Advantageously, compositions of the present invention have improved aesthetics, when compared to other hand sanitizers or health care personnel handwashes that claim to have skin conditioning properties.

Some studies have identified the four categories of sensory attributes for products: Sensory Evaluation; Acceptance Attributes; Performance (non-antimicrobial); and Image. Sub-categories of attributes include the following.

Sensory Evaluation includes: Clear; Opaque; Strong Smell; Light Smell; No Smell; Oily Feel; Dry Feel; Soft Feel; Lathers Well.

Acceptance Attributes include: Like Appearance; Like Fragrance; Like Texture; Like Feel After Use; Like Overall; Purchase Intent.

Performance (non-antimicrobial) includes: Lathers Well; Feels Good On Hands; Does Not Irritate Hands; Conditions Hands; Removes Oil From Hands; Feels Clean.

Image includes: effective; Unique; Good For Hands; Won't Ruin Gloves; Won't Irritate Hands; High Quality Product.

In one or more embodiments, panel test results indicate that compositions of the present invention provide better overall sensory scores, higher acceptance attributes, improved performance scores, and higher image ratings, when compared to other hand sanitizers or health care personnel handwashes that claim skin-conditioning effects.

d. Maintained Efficacy

Advantageously, compositions of the present invention provide skin-conditioning benefits while maintaining antimicrobial efficacy.

Thus, the present invention further provides a method for killing or inactivating microbes on a surface comprising applying, to the surface, an effective amount of an antimicrobial composition as described herein. The antimicrobial composition may be employed on a wide variety of surfaces or substrates, including skin, porous, and non-porous surfaces.

In one or more embodiments, the antimicrobial composition of the present invention is applied topically to mammalian skin. In one embodiment, the methods of bringing the antimicrobial composition into contact with a microbe on human skin includes applying an amount of the composition to the skin, and allowing the composition to remain in contact with the skin for a suitable amount of time. In other embodiments, the composition may be spread over the surface of the skin, rubbed in, rinsed off, allowed to dry via evaporation, or wiped off.

Thus, the present invention provides a method for skin sanitization, the method comprising contacting mammalian skin with an effective amount of an antimicrobial composition comprising at least 30 wt. % alcohol, based upon the total weight of the antimicrobial composition, and an efficacy-enhancing amount of at least one $C_{6-10}$ alkane diol. In one or more embodiments, the present invention provides a method for hand sanitization.

Any amount of the antimicrobial composition may be used for each application, so long as it is at least an effective amount to contact substantially the entire target surface and keep it wet for at least 15 to 30 seconds. In one embodiment, an effective amount is at least about 1.5 milliliters (mL), in another embodiment at least about 2 mL, in yet another embodiment, at least about 2.5 mL, in yet another embodiment, at least about 3.0 mL, in yet another embodiment, at least about 4.5 mL, and in yet another embodiment, at least about 5 mL. Advantageously, the effective amount of antimicrobial composition according to the present invention, i.e. the minimum amount necessary to contact substantially the entire target surface, is also an amount that is effective to achieve adequate efficacy. Other products may not achieve adequate efficacy if only an effective amount to contact substantially the entire target surface is used. It will be understood that it is advantageous to achieve adequate efficacy while using a small amount of product. This is true for economic reasons, as well as because the amount of time required for the product to be rubbed into the skin and or evaporated/dried is reduced when less product is used.

Advantageously, the antimicrobial composition of the present invention may be used as a healthcare personnel hand wash. In one or more embodiments, the present invention provides an antimicrobial composition that meets the standards of the FDA TFM test for healthcare personnel hand wash.

In the FDA TFM test for healthcare personnel hand wash and other standard tests, test procedures include multiple wash cycles. In each cycle, a subject surface is contaminated with a test organism and the surface is washed with a test product. After a specified number of wash cycles, the surface is rinsed and the rinsing liquid is tested to determine what log reduction has been achieved by the test product. For example, in the FDA TFM test for healthcare personnel hand wash, the following protocol is followed for leave on products such as alcoholic compositions. The hands of a test subject are contaminated with a test organism such as *Serratia marcescens*, and washed using the test product. The hands are then placed into sterile gloves, a bacterial recovery solution is added and hands are massaged by a technician for a preset amount of time to recover viable bacteria from the hands. The recovery solution is plated to determine the log reduction achieved by one wash. The hands of the test subject are again contaminated with the test organism and washed using the test product. For a third time the hands of the test subject are again contaminated with the test organism and washed using the test product. After the third wash the hands are again placed into gloves and viable bacteria are recovered to determine the log reduction after the third wash. The cycle of contamination and wash is repeated until, after the seventh wash, the hands are again placed into gloves and viable bacteria are recovered to determine the log reduction after the seventh wash. The cycle of contamination and wash is repeated until, after the tenth wash, the hands are again placed into gloves and viable bacteria are recovered to determine the log reduction after the tenth wash. According to the FDA TFM test for healthcare personnel hand wash, healthcare personnel hand wash formulations must reduce the number of bacteria on the hands by 2 $\log_{in}$ after one wash and reduce the number of bacteria on the hands by 3 $\log_{10}$ after ten washes. It should be noted that the FDA TFM test for healthcare personnel hand wash refers to "wash" for both rinse-off and leave-on products, and therefore the instant specification may do the same.

Many alcoholic products achieve a minimum 3 log reduction after one wash using the FDA TFM test for healthcare personnel hand wash. However, many alcoholic products fail to achieve a minimum of 3 log reduction after the tenth wash using the FDA TFM test. In fact, a number of alcoholic products exhibit a reduction in log reduction over successive washes.

Many products that tout skin-conditioning properties do not provide adequate antimicrobial efficacy in order to meet the requirements of the FDA TFM healthcare personnel hand wash test.

Advantageously, the compositions of the present invention do not exhibit a reduction in efficacy over successive washes, when tested according to the FDA TFM test for healthcare personnel hand wash or similar protocol.

In one or more embodiments, the compositions of the present invention meet or exceed the requirement of 2 $\log_{10}$ reduction after a first wash, and 3 $\log_{10}$ reduction after a tenth wash. In one or more embodiments, compositions according to the present invention provide a log reduction of at least about 3 after one wash, and at least about 3 after ten washes. In certain embodiments, the compositions demonstrate a cumulative effect and surpasses the requirements of the FDA TFM healthcare personnel hand wash test by achieving 3 $\log_{10}$ reduction after wash 1 and 4 $\log_{10}$ reduction after wash 10.

In one or more embodiments, the $\log_{10}$ reduction of a test organism achieved by a third wash utilizing the composition of the present invention is at least equal to the $\log_{10}$ reduction achieved by a first wash cycle. In one or more embodiments, the $\log_{10}$ reduction of a test organism achieved by a tenth wash utilizing the composition of the present invention is at least equal to the $\log_{10}$ reduction achieved by a first wash cycle.

When evaluated according to tests that require multiple wash cycle protocols, compositions according to the present invention provide a log reduction that is maintained or even improved over multiple wash cycles. Furthermore, the composition unexpectedly provides cumulative activity, i.e. the efficacy of the composition increases with multiple uses.

In order to demonstrate the practice of the present invention, the following examples have been prepared and tested. The examples should not, however, be viewed as limiting the scope of the invention. The claims will serve to define the invention.

EXAMPLES

I. Biomarker Testing

The samples were tested for anti-inflammatory and skin barrier effects.
Testing Methods
IL-8 ELISA Interleukin 8 (IL-8) is a chemokine and proinflammatory cytokine produced by macrophages and other cell types such as epithelial cells. It is secreted from keratinocytes in skin in response to inflammatory stimuli. IL-8 is secreted and is an important mediator of the immune reaction in the innate immune system response. IL-8 overexpressed is a biomarker of skin irritation.

For Control A, human dermal keratinocytes are left untreated. No irritation is expected, and therefore Control A provides a baseline. For Control B, IL-8 is induced in human dermal keratinocytes by applying phorbol 12-myristate 13-acetate (PMA). For all other samples, the human dermal keratinocytes are co-treated with PMA and a composition containing the ingredient of interest. Decreased 11-8 expression reflects the ingredient's anti-irritation activity.

In order to carry out the test method, an assay kit was employed that was obtained from R&D Systems: Human CXCL8/IL-8 Duoset ELISA Development Kit.

The following steps were followed: 1. Coat EIA high binding 96-well plate with IL-8 capture antibody overnight at room temperature. 2. Prepare all reagents, standard dilutions, and samples. 3. Wash the coated plate with 350 µL/well of washing buffer 4 times, then adding 300 µL/well of blocking solution incubating 1 hour at room temperature. 4. Repeat washing step with 350 µL/well of wash buffer (4 times). 5. Add 100 µL, of Standard, control, or sample to each well. Cover with a plate sealer, and incubate at room temperature for 2 hours. 6. Aspirate each well and wash, repeating the process 3 times for a total of 4 washes. 7. Add 100 µL, of detection IL-8 antibody to each well. Cover with a new plate sealer, and incubate at room temperature for 2 hours. 8. Aspirate and wash 4 times. 9. Add 100 µL, Biotin-Strepavidin conjugate to each well, incubating 20 minutes at room temperature. 10. Aspirate and wash 4 times. 11. Add 100 µL, substrate Solution to each well. Incubate at room temperature for 20 minutes, making sure to protect the wells from the light. 12. Add 50 µL, of Stop Solution to each well. Data collected-using a colorimeter, absorbance was measured at 450 nanometers (nm) within 30 minutes. Wavelength correction was set to 570 nm.

TNF-α

Samples were tested similarly to the method described above, except that TNF-α was used instead of IL-8.

MTT Assay

The MTT assay is a colorimetric assay for assessing cell viability, cell proliferation, and/or cytotoxicity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to insoluble formazan, which has a purple color. MTT assay can also be used to measure cytotoxicity (loss of viable cells) or cytostatic activity (shift from proliferative to resting status) of potential medicinal agents and toxic materials.

Controls A and B described above for the IL-8 Assay were also employed in this test. The mitigating effect of the test samples on the effect of Control B on the keratinocytes was measured. More specifically, while Control B has a negative effect on cell viability, cell proliferation, and/or cytotoxicity, this mitigation of this negative effect was determined by measuring the reduction of MTT.

The following steps were followed: Once the liquid was removed from the wells for the IL-8 Assay described above, 100 µl/well of 0.5 mg/ml of MTT in phenol red-free DMEM (cell culture medium) was added into each of the 96-well plates. After incubating 1 hour at 37° C., all liquid was removed (MTT solution) from the wells of the culture plate. Then 100 µl of DMSO was added to each well to completely dissolve the purple product. Absorption was measured using a plate reader at 550 nm wavelength.

Varying amounts of avenanthramide were prepared in cell culture medium. The avenanthramide was obtained from Ceapro Inc., under the tradename CP Oat Avenanthramides. The amounts shown in the following table are based upon the amount of active (avenanthramide). Results are shown in the Tables below.

TABLE 1

| Example # | Component | Component Amount (wt. %) | IL-8 Inhibition (%) |
|---|---|---|---|
| Control A | Medium | — | 100% |
| Control B | PMA | — | 0.0% |
| Example 1 | Avenanthramide | 0.50% | 4.37% |
| Example 2 | Avenanthramide | 0.20% | 10.36% |
| Example 3 | Avenanthramide | 0.10% | 16.37% |
| Example 4 | Avenanthramide | 0.050% | 16.68% |
| Example 5 | Avenanthramide | 0.020% | 21.17% |
| Example 6 | Avenanthramide | 0.010% | 47.83% |
| Example 7 | Avenanthramide | 0.005% | 42.34% |

TABLE 2

| Example # | Component | Component Amount (wt. %) | TNF-α Inhibition (%) |
|---|---|---|---|
| Control A | Medium | — | 100% |
| Control B | PMA | — | 0.0% |
| Example 8 | Avenanthramide | 0.10% | 37.07% |
| Example 9 | Avenanthramide | 0.050% | 43.58% |
| Example 10 | Avenanthramide | 0.020% | 44.50% |
| Example 11 | Avenanthramide | 0.005% | 58.8% |
| Example 12 | Avenanthramide | 0.002% | 53.2% |

TABLE 3

| Example # | Component | Component Amount (wt. %) | Cell Viability (%) |
|---|---|---|---|
| Control A | Medium | — | 100% |
| Control B | PMA | — | 95% |
| Example 13 | Avenanthramide | 0.020% | 92% |
| Example 14 | Avenanthramide | 0.010% | 105% |
| Example 15 | Avenanthramide | 0.005% | 93% |

Varying amounts of niacinamide were prepared in cell culture medium. The amounts shown in the following table are based upon the amount of active niacinamide. Results are summarized in the Tables below.

TABLE 4

| Example # | Component | Component Amount (wt. %) | IL-8 Inhibition (%) |
|---|---|---|---|
| Control A | Medium | — | 100% |
| Control B | PMA | — | 0.0% |
| Example 16 | Niacinamide | 0.20% | 0.0% |
| Example 17 | Niacinamide | 0.10% | 16.53% |
| Example 18 | Niacinamide | 0.050% | 16.64% |
| Example 19 | Niacinamide | 0.020% | 20.86% |
| Example 20 | Niacinamide | 0.010% | 28.85% |
| Example 21 | Niacinamide | 0.005% | 33.20% |
| Example 22 | Niacinamide | 0.002% | 32.04% |

TABLE 5

| Example # | Component | Component Amount (wt. %) | TNF-α Inhibition (%) |
|---|---|---|---|
| Control A | Medium | — | 100% |
| Control B | PMA | — | 0.0% |
| Example 23 | Niacinamide | 0.05% | 28.2% |
| Example 24 | Niacinamide | 0.020% | 29.6% |
| Example 25 | Niacinamide | 0.010% | 28.6% |
| Example 26 | Niacinamide | 0.005% | 45.6% |
| Example 27 | Niacinamide | 0.002% | 45.1% |
| Example 28 | Niacinamide | 0.001% | 52.7% |

TABLE 6

| Example # | Component | Component Amount (wt. %) | Cell Viability (%) |
|---|---|---|---|
| Control A | Medium | — | 100% |
| Control B | PMA | — | 95% |
| Example 29 | Niacinamide | 0.020% | 97% |
| Example 30 | Niacinamide | 0.010% | 95% |
| Example 31 | Niacinamide | 0.005% | 99% |
| Example 32 | Niacinamide | 0.002% | 87% |

Skin Barrier

An in vitro model was employed, using monolayer human dermal keratinocytes culture (KGM). Two controls were tested: the medium and inflammatory cytokines interleukin (IL-1b).

Skin Barrier:
  Biomarkers: ABCA12, Involucrin, PPARδ
  Using different concentration of ingredients to treat the keratinocyte for 24 hours
  Collect the cells and prepare total RNA from the treated cells
  Using Real-time RT-PCT to detect different barrier function related biomarker's gene expression level
  Comparative Benchmark: Vitamin D3 (cholecalciferol) in three different concentrations
Results are shown in the Table below.

TABLE 7

| Example # | Component | Component Amount (wt. %) | ABCA12 (%) | Involucrin | PPARδ |
|---|---|---|---|---|---|
| Control C | KGM | — | 100% | 100% | 100% |
| Comparative 1 | Vitamin D3 150 nM | — | 58% | 384% | 752% |
| Comparative 2 | Vitamin D3 100 nM | — | 45% | 208% | 334% |
| Comparative 3 | Vitamin D3 10 nM | — | 42% | 406% | 238% |
| Example 33 | Niacinamide | 0.1% | 41% | 156% | 82% |
| Example 34 | Niacinamide | 0.05% | 120% | 192% | 88% |
| Example 35 | Niacinamide | 0.02% | 192% | 441% | 136% |
| Example 36 | Niacinamide | 0.01% | 806% | 817% | 164% |
| Example 37 | Niacinamide | 0.005% | 447% | 1589% | 378% |
| Example 38 | Niacinamide | 0.002% | 499% | 1656% | 863% |

Involucrin is a protein component of human skin. It's a biomarker for keratinocyte differentiation. In binding the protein loricrin, involucrin contributes to the formation of a cell envelope that protects corneocytes in the skin stratum corneum. The higher expression, the better skin barrier function is.

ABCA12 is also known as ATP-binding cassette transporter 12. It is a protein that in humans is encoded by the ABCA12 gene. The ABCA12 gene is active in some types of skin cells. The ABCA12 protein appears to be essential for normal development of the skin, which provides a barrier between the body and its surrounding environment. It plays an important role in transporting lipids (free fat acids) in cells that make up the outermost layer of skin (the epidermis). Generally, the higher expression, the better skin barrier function is.

PPARδ is Peroxisome proliferator-activated receptor, also known as NR1C2. It is a nuclear receptor that in humans is encoded by the PPARD gene. This protein has been shown to be involved in differentiation, lipid accumulation (ceramides) in keratinocytes. Generally, the higher expression, the better skin barrier function is.

II. Healthcare Personnel Handwash

Examples 39 and 40 are commercially available hand sanitizers that contain, inter alia, ingredients that are often touted as skin-conditioning ingredients. Unfortunately, these skin-conditioning products were tested according to the FDA TFM test for healthcare personnel hand wash, and did not pass. In contrast, compositions of the present invention provide skin-conditioning benefits, and also pass the FDA TFM test for healthcare personnel hand wash. Example 41 contains the ingredients listed below. More specifically, the amount of avenanthramide was between 0.001 to about 8 wt. %, the amount of niacinamide was between 0.001 to about 8 wt. %, the amount of PPG-12 SMDI copolymer was between 0.001 to about 8 wt. %, and the total amount of other skin conditioning agents was less than about 2 wt. %, all based upon the total weight of the composition.

TABLE 8

| EXAMPLE | TEST PRODUCT | ACTIVE INGREDIENT | INACTIVE INGREDIENTS | PASS/FAIL |
|---|---|---|---|---|
| 39 | Avagard ® D | 61% ethanol (w/w) | Beheneth-10, behenyl alcohol, C20-40 pareth-24, cetyl palmitate, diisopropyl dimer dilinoleate, dimethicone, glycerin, polyethylene glycol, qualene, water | FAIL |
| 40 | Kleenex ® Moisturizing Foam Hand Sanitizer Ultra | 70% ethanol (w/w) | Aloe barbadensis leaf extract, betaine, *camellia oleifera* leaf extract, citric acid, cucumber fruit extract, isopropanol, glycerin, meadowfoamamidopropyl betaine, panthenol, PEG-10 dimethicone, water | FAIL |
| 41 | Inventive Composition | 70% ethanol (w/w) | Water, Isopropyl Alcohol, PEG-12 Dimethicone, Caprylyl Glycol, Glycerin, PEG-33, PEG-14, PEG-8 Dimethicone, Niacinamide, Sodium lactate, Sodium gluconate, *Avena Sativa* (Oat) Extract, Potassium sorbate, PPG-12 SMDI Copolymer | PASS |

In order to document the skin's moisture content, a measuring capacitor is pressed against the skin using constant pressure and the readings evaluated. The narrow diameter of the sensor even allows measurements to be taken on less accessible areas of skin. The corneometer is a fully automatic device. The reading indicates the epidermal hydration level—before and after treatment with cosmetic or pharmaceutical products, for instance. The recordings are always carried out within a constant time frame following the use of the respective product. Hydration was measured in a morning session and an afternoon session, and the change of hydration is shown below.

Trans-Epidermal Water Loss (TEWL) was measured using an Aquaflux® instrument, in units of grams of water per square meter per hour (g water/m$^2$/hr). The change in TEWL from the morning session to the afternoon session is shown below.

TABLE 9

| EXAMPLE # (wt. %) | 42 | 43 | 44 | 45 |
|---|---|---|---|---|
| SDA 3C ethanol | 74.1 | 74.1 | 74.1 | 74.1 |
| Hydrolyzed jojoba esters | 0.75 | | 0.75 | |
| Silsense Copolyol-1* | | 0.25 | | 0.20 |
| Niacinamide | 0.3 | 0.3 | 0.3 | 0.3 |
| Avenanthramides | 1 | 1 | 1 | 1 |
| PEG-75 | 0.4 | 0.3 | | |
| Glycerin | 0.25 | 0.25 | 0.2 | 0.2 |
| Purasal Moist XS | | | 1.43 | 1.43 |
| Polyolprepolymer-2 | | | 0.1 | 0.1 |

III. FCAT

The following samples were tested for irritancy according to the FCAT technique described above. Each of the examples 42-45 contained the same amount of ethanol, PEG-12 dimethicone, 1,2-octanediol, and the differing amounts of the other ingredients are shown below. The samples were made to 100% using purified water.

Corneometry, a technology that is used to measure the hydration of the outer layer of the epidermis (stratum corneum), was employed. As the skin is a dielectric medium, variations in hydration show up through changes in capacity.

TABLE 9-continued

| EXAMPLE # (wt. %) | 42 | 43 | 44 | 45 |
|---|---|---|---|---|
| Change in Hydration | 23.70 | 27.30 | 34.28 | 31.40 |
| Change in TEWL | −1.67 | −1.92 | −2 32 | −2.43 |

*Proprietary blend with INCI Name PEG-33 (and) PEG-8 Dimethicone (and) PEG-14

In comparison, a commercially available "skin-conditioning" product sold under the tradename Ecolab Quik-Care Nourishing Foam Hand Sanitizer was tested under the same conditions, and provided a Change in Hydration of 21.39 and a Change of TEWL of −1.99.

IV. Aesthetics/Tackiness

Generally, after the desired contact time, samples were tested for tack as follows. Using a Chemsultants International Probe Material Analyzer PMA-1000, equipped with a 3/16″ diameter flat probe tip, about 100 grams of force was applied onto each sample for 5 seconds dwell time, and the retraction force was measured. In most cases, multiple readings were taken and averaged. Greater specifics are provided below.

The equipment used was a Probe Material Analyzer PMA-1000 with EZ Lab Software
The procedure for a 1× Application was as follows:
Apply 1 mL of product to a metal weigh dish
Allow product to air dry for 1 hour
Place weigh boat under the spindle of the PMA, and test 3× (middle of sample, and two areas on outer edges)
View data in EZ Lab as a Positive Refraction Graph
Record the "High" measurement for each sample
The highest measurement for each sample represents the highest level of tack seen, and this is the number reported
The procedure for the 5× Application was as follows:
Apply 1 mL of product to a metal weigh dish
Allow product to air dry for 1 hour
Repeat steps 1 & 2 four times
Place weigh boat under the spindle of the PMA, and test 3× (middle of sample, and two areas on outer edges)
View data in EZ Lab as a Positive Refraction Graph
Record the "High" measurement for each sample
The highest measurement for each sample represents the highest level of tack seen, and this is the number reported
Results are summarized below.
Example 46 was prepared as follows.

TABLE 10

| Raw Material | Wt. % |
| --- | --- |
| Purified Water | 22.95 |
| Caprylyl Glycol | 0.25 |
| Bio Alcohol SDA 3C 190 | 74.10 |
| Glycerin | 0.50 |
| PEG-12 Dimethicone | 2.00 |
| Isopropyl Myristate | 0.10 |
| Tocopheryl Acetate | 0.10 |
| | 100.00 |

Example 47 was prepared by combining 95 grams of Example 46 and 5 grams glycerin.
Example 48 was prepared as follows.

TABLE 11

| Raw Material | % |
| --- | --- |
| Purified Water | 22.97 |
| Caprylyl Glycol | 0.25 |
| Bio Alcohol SDA 3C 190 | 74.10 |
| Glycerin | 0.30 |
| PEG-12 Dimethicone | 2.00 |

TABLE 11-continued

| Raw Material | % |
| --- | --- |
| Isopropyl Myristate | 0.02 |
| Tocopheryl Acetate | 0.02 |
| Niacinamide | 0.20 |
| Avenanthramide | 0.07 |
| PPG-12/SMDI Copolymer | 0.06 |
| | 100.00 |

Example 49 was a commercially available sanitizer that is sold under the moniker Cal Star® Plus Antiseptic Handrub with Enhanced Emollients by Steris Corporation. According to the label, it contains 63% v/v Isopropyl alcohol, deionized water, methylpropanediol, penoxyethanol, cetyl lactate, glycerin, hydroxypropyl cellulose, polyquaternium-6, behentrimonium methosulfate, and fragrascent power. Cetyl lactate, glycerin, polyquaternium-6, behentrimonium methosulfate are emollients/skin conditioners.

Samples were tested for tack as described above. The results (in grams) are summarized in the Table below.

TABLE 12

| Example # | 1× Application | 5× Application |
| --- | --- | --- |
| Example 46 | 6.6 | 17.3 |
| Example 47 | 14.9 | 21.4 |
| Example 48 | 2.8 | 9.4 |
| Example 49 | 26.4 | 24.3 |

Various modifications and alterations that do not depart from the scope and spirit of this invention will become apparent to those skilled in the art. This invention is not to be duly limited to the illustrative embodiments set forth herein.

We claim:

1. A foamable healthcare personnel handwash composition that maintains or improves skin hydration, the composition consisting of:
   from 50 to 98 wt. % of one or more $C_{1-6}$ alcohols;
   from 0.001 to 0.5 wt. % of avenanthramides;
   from 0.001 to 0.3 wt. % of niacinamide;
   from 0.002 to 4 wt. % of PEG-12 dimethicone, PEG-10 dimethicone, PEG-8 dimethicone, or combinations thereof;
   from 0.005 to 1.0 wt. % of polyolprepolymer-2;
   optionally, less than 1 wt. % of one or more skin conditioners selected from the group consisting of aloe, vitamin E, and diols straight chain;
   optionally, less than 1 wt. % glycerin;
   optionally, one or more essential oils;
   optionally, less than 0.1 wt. % of one or more moisturizing esters selected from the group consisting of cetyl myristate, cetyl myristoleate, and other cetyl esters, diisopropyl sebacate, and isopropyl myristate; and
   water,
   wherein each weight percentage is based upon the total weight of the composition, and
   wherein the viscosity of the composition is less than 100 cps at 22° C.

2. The composition of claim 1, wherein the diol consists of one or more $C_{6-10}$ alkane diols.

* * * * *